United States Patent [19]

Gschwind et al.

[11] Patent Number: 5,462,608
[45] Date of Patent: Oct. 31, 1995

[54] PELTIER EFFECT DEVICE TO DETECT IN PARTICULAR A CONDENSATION RISK ON A SURFACE BEING IN CONTACT WITH A WET AIR VOLUME

[75] Inventors: Michel Gschwind, Grasse; Pascal Ancey, Le Rouret, both of France

[73] Assignee: Imra Europe SA, Valbonne, France

[21] Appl. No.: 222,267

[22] Filed: Apr. 4, 1994

[30] Foreign Application Priority Data

Apr. 6, 1993 [FR] France ................... 93 04058

[51] Int. Cl.$^6$ .................. H01L 35/10; H01L 35/32
[52] U.S. Cl. .............................. 136/203; 136/225
[58] Field of Search ........................ 136/203, 204, 136/225

[56] References Cited

U.S. PATENT DOCUMENTS

| | | | |
|---|---|---|---|
| 3,405,271 | 10/1968 | Stevens et al. | 250/83.3 |
| 3,405,272 | 10/1968 | Stevens et al. | 250/83.3 |
| 3,405,273 | 10/1968 | Stevens et al. | 250/83.3 |
| 3,554,815 | 1/1971 | Osborn | 136/203 |
| 3,981,751 | 9/1976 | Dashevsky et al. | 136/225 |
| 4,049,469 | 9/1977 | Kolomoets et al. | 136/225 |
| 4,197,738 | 4/1980 | Degenne | 73/190 |
| 4,343,960 | 8/1982 | Eguchi et al. | 136/225 |
| 4,677,416 | 6/1987 | Nishimoto et al. | 338/35 |
| 4,859,250 | 8/1989 | Buist | 136/225 |

FOREIGN PATENT DOCUMENTS

| | | | |
|---|---|---|---|
| 2238252 | 2/1975 | France | 136/225 |
| 3707631 | 9/1988 | Germany | 136/225 |
| 58-171873 | 10/1983 | Japan | 136/225 |

OTHER PUBLICATIONS

Ikuo Nishimoto, "Humidity Detection Element", Patent Abstracts of Japan, vol. 10, No. 312, (P–509); Oct. 23, 1986 & JP–A–61 124 857.

Primary Examiner—Donald P. Walsh
Assistant Examiner—Chrisman D. Carroll
Attorney, Agent, or Firm—Foley & Lardner

[57] ABSTRACT

A Peltier effect device which detects in particular a condensation risk, includes a substrate and semiconducting bands disposed on the upper face of the substrate. The junctions connecting said bands which make up a series circuit are formed by semiconducting bands of N-type and P-type. Junctions of the same type, i.e., N-P type are situated on the central zone of the upper face of the substrate and defines a detection zone of the device. Semiconducting bands of one type are placed on one side of the upper face of the substrate and bands of the other type are placed on the other side of the upper face of the substrate. The substrate also includes at the peripheral zone of each band, except for a frontmost N-type band and a rearmost P-type band, a plated hole extending through the substrate to a lower face of the substrate and to a plating of the lower face such that a plated hole situated at an end of the P-type band is connected to a plated hole situated at an end of a next N-type band.

8 Claims, 3 Drawing Sheets

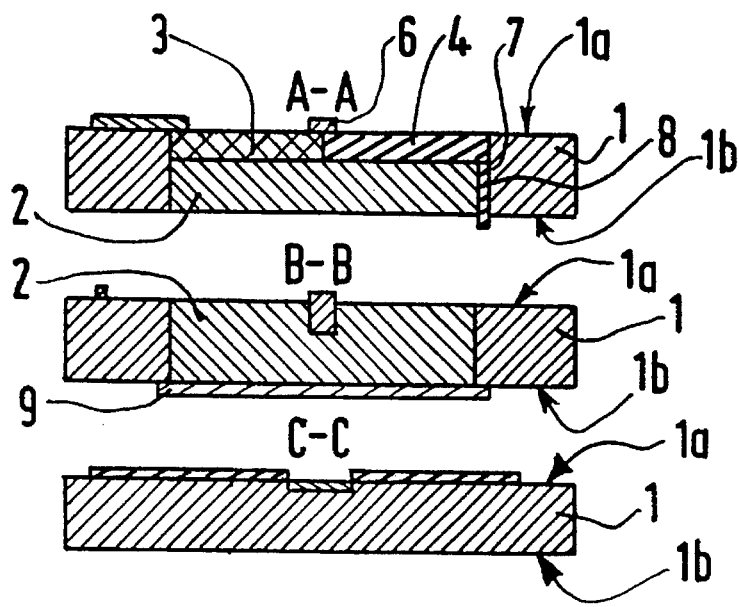
FIG. 1A
FIG. 1B
FIG. 1C
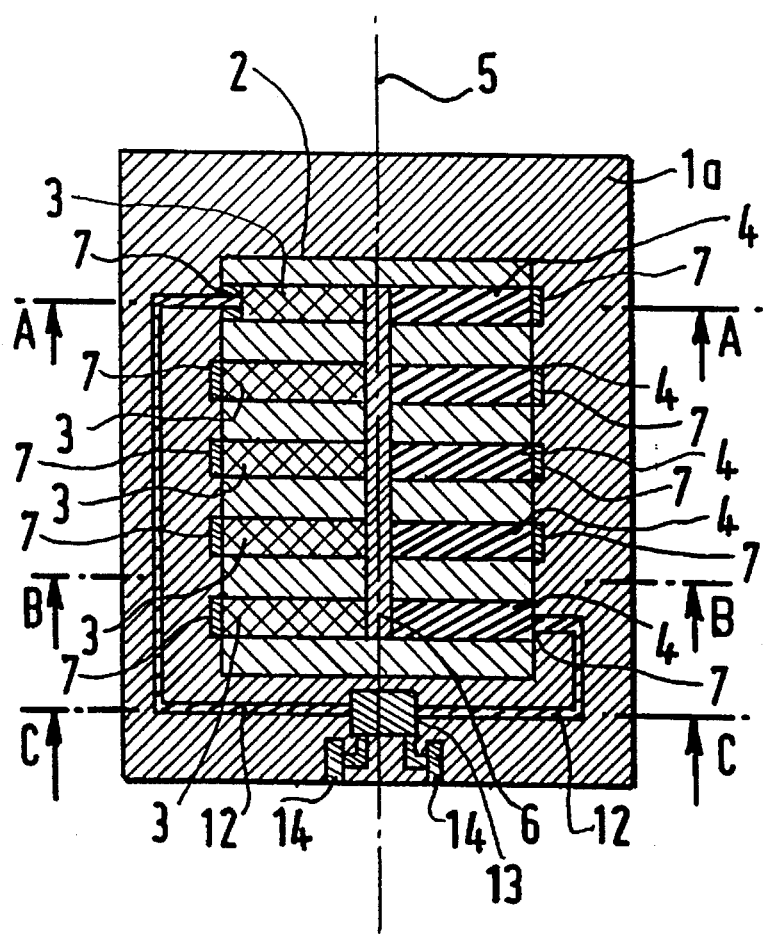
FIG. 1

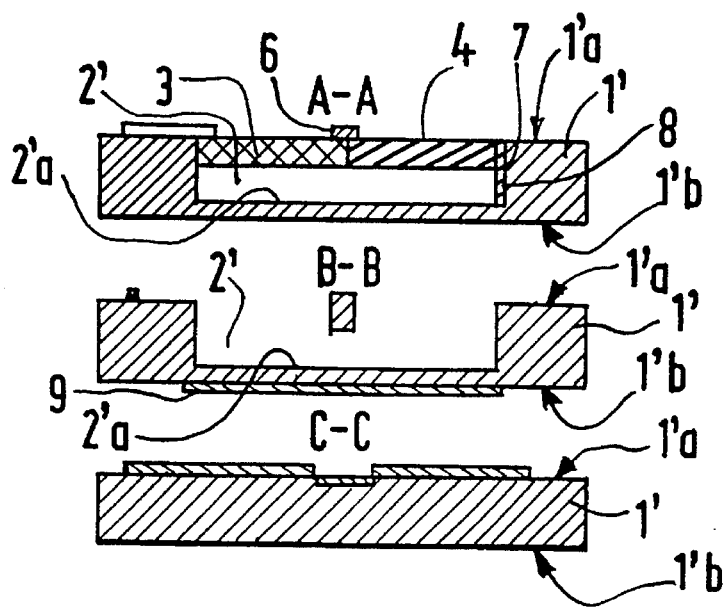
FIG. 4A
FIG. 4B
FIG. 4C
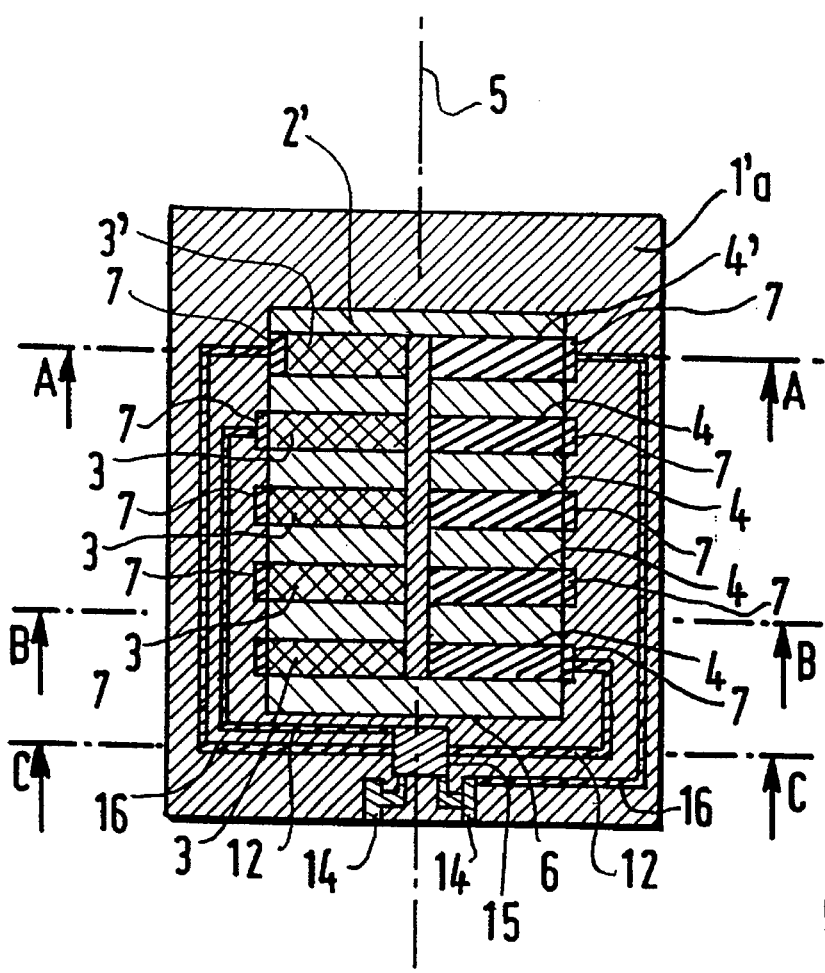
FIG. 4

PELTIER EFFECT DEVICE TO DETECT IN PARTICULAR A CONDENSATION RISK ON A SURFACE BEING IN CONTACT WITH A WET AIR VOLUME

BACKGROUND OF THE INVENTION

The present invention concerns a Peltier effect device aiming in particular at detecting a condensation risk on a surface being in contact with a wet air volume.

Devices which detect the dew-point temperature and the ambient air relative humidity are already known.

The U.S. Pat. No. 4,677,416 document describes a device with a substrate on the upper face of which two semiconducting PbTe bands, alternately of N-type and P-type, are mainly formed. The bands extend between a peripheral zone and a central zone of the upper face of the substrate, and are connected in series by N-P and P-N type junctions and constitutes a circuit alternately formed of N-type bands and P-type bands. All N-P type junctions are situated in the central zone of the substrate, and all P-N type junctions are situated in the peripheral zone of the substrate.

In such a device, when current passes in the series circuit, the central zone of the substrate is cooled down by the Peltier effect. A quantity of heat is absorbed by the junctions present in the central zone of the substrate and released with an approximate amount equivalent to the Joule effect, by the junctions present in the peripheral zone of the substrate.

However, the efficiency of this device may prove to be insufficient because the peripheral junctions are situated on the same face of the substrate as the detection zone, such that while the detection zone is cooled down by the Peltier effect, it may receive a part of the thermal energy released by the peripheral junctions.

Besides, this thermal energy is mainly transmitted by conduction in the thickness of the substrate before being dissipated.

Such inconveniences do not really matter in case of a dew-point temperature measurement, but when a condensation risk has to be detected, for instance by implementing the process described in the unpublished patent application No. 93 02099 of the requesting party, it is better to have a Peltier effect device which is able to quickly dissipate the thermal energy released by the junctions situated outside the detection zone, such that the detection zone is not subject to the influence of such dissipation.

SUMMARY OF THE INVENTION

The present invention aims at providing a Peltier effect device, particularly fit for the implementation of a process of detection of condensation risk on a surface in contact with a wet air volume, which has the advantages of quickly dissipating the thermal energy released by the junctions placed outside the detection zone and of thermally decoupling this detection zone from the junctions placed outside the detection zone.

In addition, the device according to the invention includes a detection zone with a favorably weak thermal mass compared to that of the zone of the substrate where the dissipation of energy, released by the junctions situated outside the detection zone, occurs.

Thus, the thermal inertia of the detection zone is weak enough to allow the zone to react promptly and with an optimal thermal efficiency, to any heating or cooling produced by the central junctions of the substrate when electric current is supplied to them, such that electricity consumption is reduced.

Furthermore, the realization mode of the device according to the invention is particularly easy and economical.

An object of the present invention is to provide a Peltier effect device, notably for the detection of a condensation risk on a surface in contact with a wet air volume, which includes substrate on which semiconducting bands of N and P types are formed and extends between a peripheral zone and a central zone of the upper face of the substrate. The semiconducting bands are connected by N-P and P-N type junctions in a series circuit formed alternately by N-type bands and P-type bands. All the N-P junctions are situated in the central zone of the upper face of the substrate and form a detection zone of the device, wherein the N-type semiconducting bands are placed on one side of the upper face of the substrate while the P-type semiconducting bands are placed on the other side of the upper face of the substrate. The substrate includes at an end of each band situated in the peripheral zone, a plated hole going through the substrate and emerging on the lower face of the substrate. A plating of its lower face forms junction bands which connect a crossing hole situated at an end of a P-type band to another crossing hole situated at an end of a next N-type band.

It is understood that the platings going right through the substrate and extending on its lower face almost parallel to the semiconducting bands placed on its upper face, make up junctions of the same type (for instance P-N) which, if associated to the junctions (for instance of N-P type) present in the detection zone of the substrate, form a Peltier element and produce thermal exchanges between the central zone of the substrate and the outside of the said substrate.

The junctions present in the central zone of the substrate upper face are preferably covered with an electrically insulating and thermally conductive material to form the detection zone of the device according to the invention.

As explained before, the thermal mass of this material is weak, so that the detection zone can react properly to the thermal stresses of the central junctions.

According to a preferred embodiment of the invention, the semiconducting bands are realized by thermal diffusion of impurities in silicon. For this purpose, arsenic and boron may be used as impurities.

It is preferable to realize a high doping (of the order of $10^{19}$ carriers per $cm^3$), which has the following two advantages.

First, since the electrical conductivity of the semiconducting bands is much higher than that of silicon (which has only approximately $10^{10}$ carriers per $cm^3$), there is practically no risk of electric leakage in the substrate.

Second, the contact between the N-type bands and the P-type bands is of good quality and it is not necessary to overdope silicon at the junction level to get a ohmic-type contact.

In order to thermally insulate the junctions present on the upper face of the substrate from the junctions present on the lower face, it is possible, according to a first variation, to place a thickness of an electrically and thermally insulating material, for instance a silicon oxide $SiO_2$, in the central part of the substrate, this central part extending preferably not further than the holes within the substrate.

It is indeed preferable to realize the crossing holes in the thermally conductive zone of the substrate, in order to make easier the transfer and dissipation of thermal energy released in the platings of the crossing hole, although this thermal energy is not dominant if compared to the energy released by the junctions placed on the lower face of the substrate.

According to a second variation, the central part of the upper face of the substrate may be hollowed out to a given thickness, in order to separate the semiconducting bands from the bottom of the cavity by an air layer serving thus as a thermal insulator.

The result is a better output of the device and an optimal decoupling between the detection zone and the junctions placed outside this detection zone.

It is clear that, due to the surface of the junctions placed on the lower face of the substrate, the thermal energy released by these junctions may be directly transmitted by conduction to a radiator on which the substrate is placed, such that the radiator secures the dissipation of this energy by convection.

In order to detect a condensation risk on a surface, the lower face of the device according to the invention is placed against the surface which acts as a radiator by realizing thermal exchanges with the junctions situated on the lower face of the substrate.

In addition, due to the compactness of the device according to the invention, if there is no electric current circulating in the Peltier circuit, the whole substrate is of a homogeneous temperature which is that of the surface on which a condensation risk is detected.

In this way, the process of detection may be implemented knowing that the initial temperature of the detection zone is essentially the same as that of the surface.

Besides, due to the fact that all the N-type semiconducting bands are arranged on one side of the substrate whereas all P-type semiconducting bands are arranged on the other side of the substrate, the technical realization of the device according to the invention is easy.

Indeed, one needs only to make a thermal diffusion of an impurity, for instance arsenic, to form a N-type layer sensibly rectangular on one side of the substrate upper face, and then form N-type bands by photo etching. The same process is used for the P-type bands, by diffusing, for instance, boron.

In a preferred embodiment of the invention, the junctions present in the central zone of the substrate upper face are also realized by surface plating, by covering the nearby ends of the N-type and P-type semiconducting bands.

Preferably, the substrate may also include other electronic circuits allowing the implementation of a process to determine a condensation risk, namely the one described by the requesting party in its unpublished patent application No. 93 02099.

In particular, the substrate may integrate an amplification stage to provide amplified voltage signals to the terminals of the series circuit formed on the substrate, in order to analyze these signals and to conduct the process of detection.

According to another embodiment of the invention, one of the junctions of the detection zone is reserved to the realization of a thermocouple, while the other junctions are connected, as described above, to form the Peltier circuit.

The thermocouple thus realized allows the measurement of temperature of the detection zone during the execution of the detection process.

This realization mode is advantageous because the thermocouple does not require a specific realization stage. Actually, the thermocouple results from the same thermal diffusion and photo etching operations as the other junctions. It is only necessary to make an additional surface plating connecting the terminals of this thermocouple to those of the electronic circuit, for instance, on the substrate.

In a preferred embodiment of the invention, the substrate is covered with a protective layer, thermally and electrically insulating, made of, for instance, Silicon nitride $Si_3N_4$.

BRIEF DESCRIPTION OF THE DRAWINGS

Aiming at a better understanding of the invention, we are going to describe now a realization mode, given as a non-restrictive example, referring to the attached drawings in which:

FIG. 1 is a top view of a Peltier effect device according to the invention, not covered with a protective layer, FIGS. 1A, 1B, and 1C are respectively cross sections according to A—A, B—B and C—C of FIG. 1, FIGS. 4, 4A, 4B and 4C are views, similar to FIGS. 1, 1A, 1B and 1C, of a device according to another realization mode of the invention.

DETAILED DESCRIPTION OF THE PREFERRED EMBODIMENTS

Figure 2A:
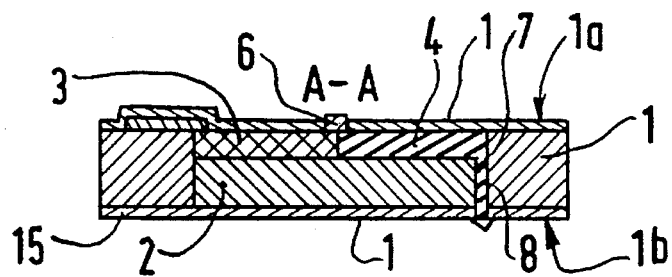
FIG. 2A is a cross section according to A—A of FIG. 2.

The device according to the invention is presented here as a rectangular plate 1 with an upper face 1a and a lower face 1b.

The plate 1 constitutes a substrate made with an electrically insulating and thermally conductive material such as silicon.

In its central part, the plate 1 includes a rectangular cavity 2 extending from its upper face 1a to its lower face 1b, and is filled up with a thermally and electrically insulating material such as silicon oxide $SiO_2$.

On the upper face 1a of the substrate, above the thermally and electrically insulating material, semiconducting bands of N-type 3 and P-type 4 have been formed by thermal diffusion of arsenic and boron.

These bands extend from the median axis 5 of the substrate 1 to the thermally conductive peripheral zone of the substrate.

The semiconducting bands of N-type 3 and P-type 4 are arranged symmetrically with respect to the median axis 5. All the N-type bands 3 are on one side of axis 5, while all P-type bands 4 are on the other side of the median axis 5.

The semiconducting bands have been formed by thermal diffusion of ions on a rectangular part extending on the corresponding side of the substrate upper face 1a, each layer having been then photo etched. In FIG. 1A, a vertical junction between the N-type band 3 and P-type band 4 is represented.

In practice, it may be difficult to realize such a vertical junction. It is then preferred according to a variation of the invention, to space out the ends of the bands 3 and 4 and to form a junction by application of a surface plating partly covering the end of the said bands 3 and 4.

Besides, the junctions between N-type bands 3 and P-type bands 4 are covered with a band 6 of an electrically insulating and thermally conductive material extending along the median axis 5.

The material of the band 6 may advantageously be the same as that which forms the peripheral zone of the substrate 1. The band 6 will preferably have a weak thermal mass as already explained.

The upper face of the band 6 constitutes the detection zone which is subject to heating and cooling phases when the process of detecting a condensation risk is implemented.

At ends of the bands 3 and 4 adjacent to peripheral zone of the substrate 1, crossing holes 7 are made, joining the upper face 1a of the substrate to its lower face 1b.

The crossing holes 7 include a volume plating 8 to electrically connect the semiconducting bands 3 and 4.

On the lower face 1b of the substrate, electrically conductive bands 9 are realized by plating and photo etching of the lower face 1b of the substrate.

Figure 3:
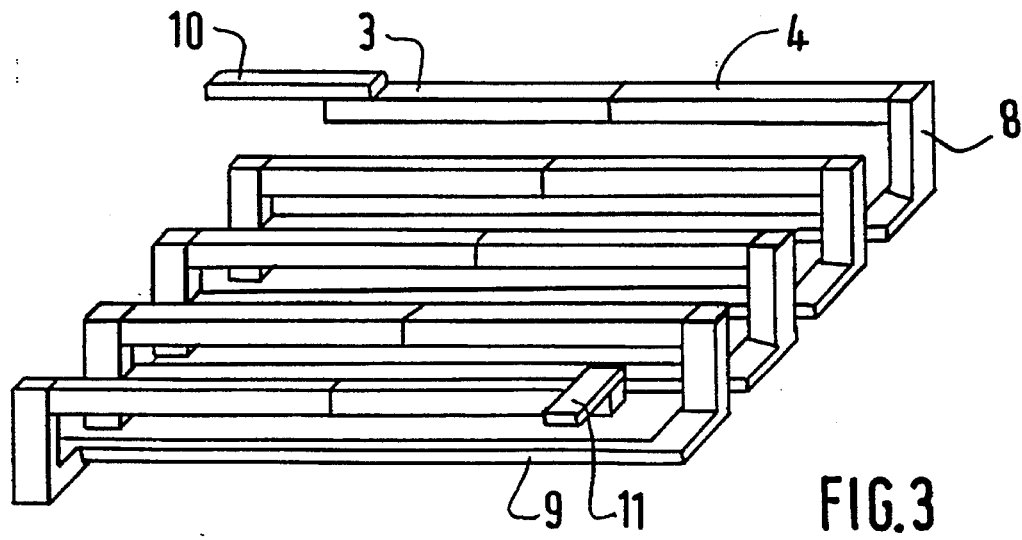
FIG. 3 is a perspective representation of the arrangement of semiconducting bands and of the junctions of the described device.

The bands 9 join the crossing holes 7 situated at an end of the N-type semiconducting band 3 to the crossing holes 7 situated at an end of the P-type semiconducting band 4, as it can be more clearly seen in FIG. 3.

It is understood that the volume platings 8 and the surface platings 9 constitute the junctions which, combined with the junctions formed on the upper face of the substrate, form the heating and cooling parts of a Peltier effect series circuit which includes sequentially a N-type band 3, a N-P junction, a P-type band 4, a P-N junction and so on.

Due to the presence of the thermally insulating material in the cavity 2, the junctions of the upper and lower faces are thermally decoupled.

One can clearly see that the junctions formed by the platings 9 which extend on the lower face 1b of the substrate can efficiently transmit their thermal energy to a radiator against which they are applied, or to a surface on which the condensation risk has to be detected.

The terminals 10 and 11 of the Peltier circuit are connected, by means of platings 12, to an integrated circuit 13 also realized on the substrate. This circuit 13 may integrate notably an amplification stage to supply an amplified signal of the voltage present at the terminals 10, 11 of the Peltier effect series circuit. Power supply contacts 14 are formed on the upper face 1a of the substrate and allow to connect the device to an electric power source.

Figure 2:
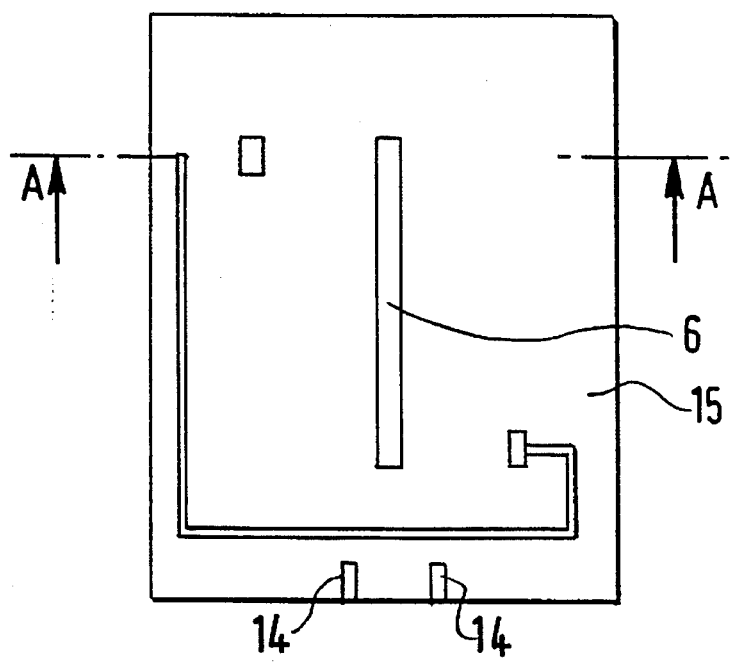
FIG. 2 is a view similar to FIG. 1, except that the device is covered with a protective layer.

As represented in FIGS. 2 and 2A, the device thus realized may include a protective layer 15, for instance, of silicon nitride $Si_3N_4$, covering its lower face 1b and its upper face 1a except for the detection band 6 and the power supply contacts 14 that have to stay in open air for the electric connection of the device according to the invention.

In a non illustrated variation, the N-type 3 and the P-type 4 bands could be radially distributed on a circular shaped substrate, which would allow to realize a dot-shaped detection zone 6 situated at the center of the said substrate and having consequently a very limited surface, and thus allowing an even greater reduction of its thermal mass.

The FIGS. 4, 4A, 4B and 4C represent a realization mode of the invention in which the central cavity 2' does not extend down to the whole thickness of the substrate 1' but includes a bottom 2'a.

The cavity 2' has been hollowed on the upper face of the substrate 1' after N-type 3 and P-type 4 bands were formed.

An air layer separates the semiconducting bands 3 and 4 from the substrate 1' and constitutes a thermal insulator allowing to decouple the detection zone from the junctions 8 and 9.

FIG. 4 also illustrates a particular realization mode, compatible with the description mode of FIGS. 1 and 2 according to which one of the central junctions is used outside the Peltier circuit as a thermocouple.

To that purpose, the bands 3' and 4', the junction of which is also covered by the band 6, are directly connected to the integrated circuit 13 by platings 16.

Thus, it is possible to conduct a detection process such as the one described in the patent application No. 93 02099 of the requesting party by controlling the exact values of temperature of the detection zone of the device. Due to the integrated circuit, it is possible to correct the possible temperature drifts of this detection zone with respect to the initial temperature of the surface on which a condensation risk is detected.

It is obvious that the realization modes which have just been described, are not restrictive and that they may undergo any desirable modification without departing from the spirit or the scope of the invention.

We claim:

1. A Peltier effect device for detecting in particular a condensation risk on a surface in contact with a wet air volume, comprising:

a substrate on which semiconducting bands of N-type and P-type are formed, each of said bands extending between a peripheral and a central zone of the upper face of the substrate, said bands being connected by junctions of N-P type and P-N type in order to make up a series circuit formed alternately of the N-type semiconducting bands and the P-type semiconducting bands, junctions of only one type being situated on the central zone of the upper face of the substrate and forming a detection zone of the device, wherein the N-type semiconducting bands are placed on one side of the upper face of the substrate and the P-type semiconducting bands (4) are placed on the other side of the upper face of the substrate and wherein the substrate has at the peripheral zone of each band except for a frontmost N-type band and a rearmost P-type band, a plated hole extending through the substrate to a lower face of the substrate and to a plating of the lower face such that a plated hole situated at an end of the P-type band is connected to a plated hole situated at an end of a next N-type band (3).

2. A Peltier effect device according to claim 1, wherein the junctions present in the central zone of the upper face of the substrate are covered with an electrically insulating and thermally conductive material.

3. A Peltier effect device according to claim 1, wherein the substrate is made of silicon and the semiconducting bands of N-type and P-type are made with silicon doped by thermal diffusion of impurities selected from a group comprising arsenic and boron.

4. A Peltier effect device according to claim 1, wherein the substrate has an electrically and thermally insulating material formed at a center portion.

5. A Peltier effect device according to claim 1, wherein the substrate has a cavity formed at a center starting from the upper face of the substrate and extending deeper than the semiconducting bands, said semiconducting bands being isolated from a bottom of the cavity by an air layer.

6. A Peltier effect device according to claim 1, wherein the junctions present in the central zone of the upper part of the substrate are formed by surface platings which partly cover ends of the semiconducting bands.

7. A Peltier effect device according to claim 1, further including two semiconducting bands electrically insulated from the series circuit to form a thermocouple.

8. A Peltier effect device according to claim 4, wherein the electrically and thermally insulating material is silicon oxide.

* * * * *